(12) United States Patent
Tabbi et al.

(10) Patent No.: US 12,112,835 B2
(45) Date of Patent: Oct. 8, 2024

(54) METHOD AND COMPUTER SYSTEM FOR DETERMINING POLYMERIC PRODUCT PROPERTIES

(71) Applicant: COVESTRO INTELLECTUAL PROPERTY GMBH & CO. KG, Leverkusen (DE)

(72) Inventors: Giuseppe Tabbi, Düsseldorf (DE); Christian Windeck, Viersen (DE); Karin Clauberg, Solingen (DE); Michael Loof, Leverkusen (DE); Roger Scholz, Selfkant-Süsterseel (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 832 days.

(21) Appl. No.: 17/253,701

(22) PCT Filed: Jun. 11, 2019

(86) PCT No.: PCT/EP2019/065243
§ 371 (c)(1),
(2) Date: Dec. 18, 2020

(87) PCT Pub. No.: WO2019/243114
PCT Pub. Date: Dec. 26, 2019

(65) Prior Publication Data
US 2021/0265023 A1    Aug. 26, 2021

(30) Foreign Application Priority Data
Jun. 18, 2018 (EP) .................................... 18178181

(51) Int. Cl.
*G16C 20/30* (2019.01)
*G16C 20/70* (2019.01)
(Continued)

(52) U.S. Cl.
CPC ............. *G16C 20/30* (2019.02); *G16C 20/70* (2019.02); *G16C 20/90* (2019.02); *G16C 60/00* (2019.02)

(58) Field of Classification Search
CPC ........ G16C 20/30; G16C 20/70; G16C 20/90; G16C 60/00
See application file for complete search history.

(56) References Cited

U.S. PATENT DOCUMENTS

2004/0242718 A1* 12/2004 Tu .................................. 521/155
2005/0038538 A1*  2/2005 McDonald, Jr. ........ G06F 19/00
                                                                  700/97
(Continued)

FOREIGN PATENT DOCUMENTS

| CN | 102409496 B | * | 5/2014 | ............. D06B 19/00 |
| EP | 1158450 A2 | * | 11/2001 | ............. G06F 17/50 |
| WO | 02/77772 A2 | | 10/2002 | |

OTHER PUBLICATIONS

Mihlayanlar E. et al: "Analysis of the effect of production process parameters and density of expanded polystyrene insulation boards on mechanical properties and thermal conductivity", Materials and Design, London, GB, vol. 29, No. 2, Oct. 24, 2007 (Oct. 24, 2007), pp. 344-352.

(Continued)

*Primary Examiner* — Catherine T. Rastovski
*Assistant Examiner* — Lal C Mang
(74) *Attorney, Agent, or Firm* — The Webb Law Firm

(57) ABSTRACT

The invention relates to a method for determining polymeric product properties (1), wherein a prediction model (7) is provided for calculating polymeric product properties (1) based on production parameters on a computer system, which production parameters comprise formulation portions (2) specifying raw material portions for polymeric production and comprise processing parameters (3) specifying process properties during polymeric production, wherein user input is provided to the computer system, which user input comprises user production parameters (4) specifying a set of production parameters, user product parameters (5) specifying polymeric product properties and a proximity metric for quantifying conformity with the user product parameters (5), wherein the computer system applies the user production parameters (4) to the prediction model (7) to calculate resultant product properties (8), wherein the computer system applies the proximity metric to the resultant product properties (8) with respect to the user product parameters (5) to determine at least one proximity value indicating a match between the user product parameters (5) and the resultant product properties (8). The invention also (Continued)

Figure 1:
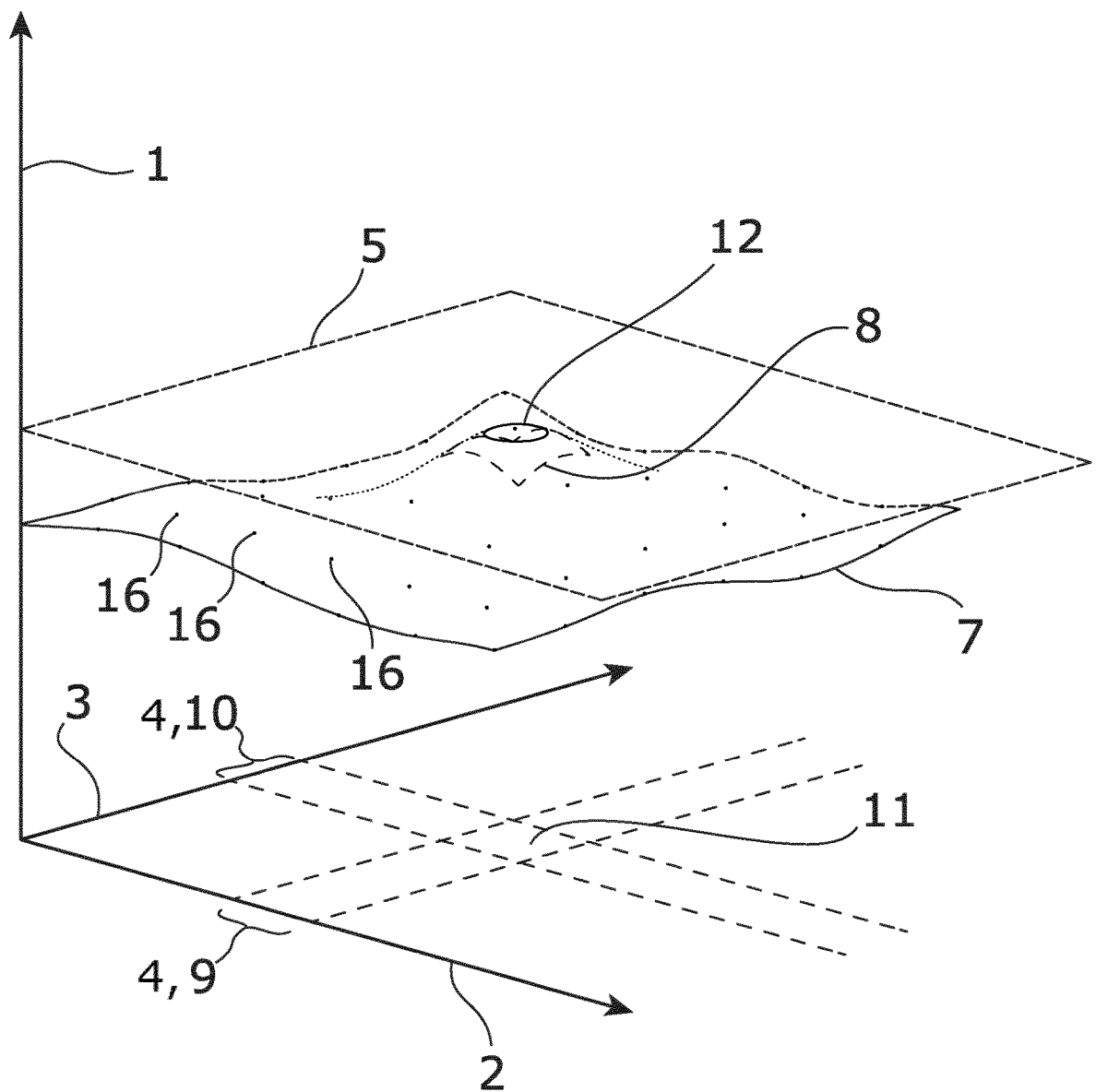

relates to a corresponding computer system for determining polymeric product properties.

15 Claims, 2 Drawing Sheets

(51) Int. Cl.
*G16C 20/90* (2019.01)
*G16C 60/00* (2019.01)

(56) References Cited

U.S. PATENT DOCUMENTS

| | | |
|---|---|---|
| 2006/0031027 A1 | 2/2006 | Alman |
| 2012/0271600 A1* | 10/2012 | Ibay ............... G16C 20/30 703/2 |
| 2015/0148514 A1 | 5/2015 | Day et al. |
| 2018/0149634 A1* | 5/2018 | Dattilo ............ G06Q 10/06 |

OTHER PUBLICATIONS

International Preliminary Report on Patentability received for PCT Patent Application No. PCT/EP2019/065243, mailed on Dec. 30, 2020, 8 pages.

International Search Report and Written Opinion received for PCT Patent Application No. PCT/EP2019/065243, mailed on Jun. 17, 2020, 10 pages.

\* cited by examiner

METHOD AND COMPUTER SYSTEM FOR DETERMINING POLYMERIC PRODUCT PROPERTIES

CROSS-REFERENCE TO RELATED APPLICATIONS

This application is a national stage application (under 35 U.S.C. § 371) of PCT/EP2019/065243, filed Jun. 11, 2019 which claims benefit of European Application No. 18178181.6, filed Jun. 18, 2018, both of which are incorporated herein by reference in their entirety.

The invention is directed at a method for determining polymeric product properties and at a computer system for determining polymeric product properties.

There is a wide range of different applications for polymeric products. Here and thereinafter polymeric products are products substantially consisting of polymeric material, i.e. one or more polymers. Consequently, there are also wide-ranging and strongly varying different product property specifications that are prescribed for those polymeric products. These different specifications determine desired values or value ranges for weight, rigidity, emissions, temperature durability and many other features of the respective polymeric product. Further, the polymeric product properties do not only depend on the formulation, which specifies the material ingredients of the polymeric product, used for the polymeric product, but also on different process parameters applied in the production process of the polymeric product, including properties of production tools used.

The interdependencies between both the specific formulations and the process parameters used and the properties of the resulting polymeric product are very complex. Though there are some theoretical considerations that provide general formulas for some correlations between ingredients of the formulation or process parameters on the one hand and polymeric product properties on the other hand, these play a relatively minor role in determining a new formulation with corresponding process parameters in order to obtain a polymeric product according to a particular product specification. Instead, the usual process involves proceeding from a known formulation and known process parameters resulting in a product with known properties and then making adjustments based on prior experience and general considerations. Based on these adjustments, a number of sample products are produced and their relevant properties experimentally determined. Based on this approach, often a cycle of trial and error is repeated until the desired product properties are sufficiently reached or approximated. It is evident that this process is both costly in terms of production time and effort and also unreliable in that due to it being substantially unsystematic, the likelihood of approximating the desired specification within a given number of sample production runs is very hard to gauge. Proceeding from this prior art approach, it is therefore desirable to improve the process such that the knowledge from past formulations can be used such that a user is able to predict the material properties of a product from a new formulation and/or new process parameters.

Consequently, the object of the invention is to provide a method and a computer system for determining polymeric product properties which permits a more precise determination of these product properties without actually producing the product based on the formulation in question with the process parameters in question.

With respect to the method for determining polymeric product properties, the object of the invention is achieved by a method for determining polymeric product properties with the features as described herein.

With respect to the computer system for determining polymeric product properties, the object of the invention is achieved by a computer system for determining polymeric product properties with the features as described herein.

The invention is based on the realization that cycles of trial and error can be reduced by utilizing a numerical prediction model which permits to arrive at an output of calculated product properties based on formulation data and process parameters that are input. By defining a specification of desired product properties as well as a metric for quantifying the degree of approximation to those desired product properties, a variety of formulation data and process parameters can be "tested" by the prediction model and a narrower determination of those formulations and associated process parameters can be arrived at such that fewer samples-namely those most closely approximating the specification-need to be actually produced and verified. Thus, development time and production costs are reduced.

The method according to the invention is for determining polymeric product properties, wherein a prediction model is provided for calculating polymeric product properties based on production parameters on a computer system. In other words, the prediction model is either a computer program or a parameter set for a computer program, which computer program is executed on a computer arrangement and which takes at least the production parameters as input and provides at least the polymeric product properties as output. Any electronic arrangement with a microprocessor presents a computer arrangement in the present sense.

In particular, the production parameters are for the production of a polymeric product. In principle, a polymeric product may be any product substantially consisting of one or more different polymer materials. Thus polymeric product properties may be the properties of any polymeric product and polymeric production may refer to the production of any polymeric product.

The polymeric product may be a polyurethane product or a polyisocyanurate product. Thus, the polymeric product properties may be polyurethane or polyisocyanurate product properties, the polymeric production may be polyurethane or polyisocyanurate production and the polymeric formulation may be polyurethane or polyisocyanurate formulation. Alternatively or in addition, the polymeric product may be a foam product. Thus alternatively or in addition, the polymeric product properties may be foam product properties, the polymeric production may be foam production and the polymeric formulation may be foam formulation.

Preferably, the polymeric product is a polycarbonate product. Accordingly, the polymeric product properties may be polycarbonate product properties, the polymeric production may be polycarbonate production and the polymeric formulation may be polycarbonate formulation.

In the method according to the invention, the production parameters comprise formulation portions specifying raw material portions for polymeric production. In other words, the formulation portions specify what raw material is used and to what proportion for producing a polymeric product. This also relates to material such as blowing agents which may be used in the production of the polymeric product but substantially are not part of the polymeric product. The production parameters may further comprise calculated/simulated data taken from formulation portions and properties of the chemical components such as density and/or hydroxyl value.

In addition, the production parameters may also comprise formulation description data for describing dynamic behavior of the raw material portions. For example, if the polymeric production is a foam production and the foam is created by the reaction of the raw materials according to the raw material portions, then the formulation description data may describe properties relating to that reaction. Thus, the formulation description data may specify starting time, rising time and/or setting time. Also, in case of a polyurea or polyurethane foam product the formulation description data may specify urea—or urethane portions and/or urea—and urethane knot density.

In the method according to the invention, the production parameters also comprise processing parameters specifying process properties during polymeric production. Preferably, the processing parameters comprise machine processing parameters specifying machine process properties during polymeric production. In the present sense, a machine may be any kind of apparatus and in particular a lab apparatus for any or all steps of polymeric production. The machine processing parameters may comprise settings for the machine or group of machines that processes the raw material in order to obtain the polymeric product. The machine processing parameters may also comprise constant characteristics of the machine or group of machines. These may include geometrical dimensions, maximum power etc. of the machine or group of machines.

It is preferred that the processing parameters comprise ambient processing parameters specifying ambient properties during polymeric production. Such ambient properties may describe any physical property the ambient environment such as temperature, pressure or moisture which may be detected by a respective sensor.

Further in the method according to the invention, user input is provided to the computer system, which user input comprises user production parameters specifying a set of production parameters, user product parameters specifying polymeric product properties and a proximity metric for quantifying conformity with the user product parameters. The set of polymeric production parameters defines a plurality of polymeric products, i.e. at least two different polymeric products. Thus the set of polymeric production parameters comprises for at least one production parameter variable at least two production parameter values.

In other words, the user input provides the above-mentioned input parameters-formulation portions and processing parameters—for the prediction model as well as desired properties of the projected polymeric product and rules in order to determine a degree of conformity between the user product parameters of the user input on the one hand and either calculated or measured product properties on the other hand. Such a metric may also take the form of a function with only two possible output values corresponding to positive conformity and lack of conformity. The user product parameters may also refer to value brackets instead of specific individual values.

According to the method of the invention, the computer system applies the user production parameters to the prediction model to calculate resultant product properties and the computer system applies the proximity metric to the resultant product properties with respect to the user product parameters to determine at least one proximity value indicating a match between the user product parameters and the resultant product properties. Thus, an indication is obtained how closely a polymeric product according to the user production parameters is projected to match the specification of the user product parameters. Depending on that indication, the user production parameters may be used for the actual production of a polymeric sample, either in a lab or in a larger scale production environment. Alternatively or in addition, the user product parameters may be used as the next starting point for searching further for suitable user production parameters or may be discarded and not used for actual production.

Applying the user production parameters to the prediction model may also comprise the prediction model determining and in particular calculating derived or intermediate values based on the user production parameters. These derived or intermediate values may then be used to calculate the resultant product properties in the same way as the user production parameters.

The polymeric product properties may in principle relate to any physical or chemical property of the polymer product resulting from the production parameters. In particular, the polymeric product properties may comprise density, compression characteristics, restoring characteristics, compression hardness, thermal conductivity, compressive strength, torsional stiffness and/or flame resistance. According to a preferred embodiment of the method, the formulation portions concern a plurality of user-selected raw materials from a list of raw materials predefined in the computer system, thereby defining combinations of the user-selected raw materials for a polymeric formulation, and the computer system applies the user production parameters to the prediction model such that for the defined combinations of the user-selected raw materials resultant product properties are calculated. Thus the user may choose raw materials from those for which the input model has information in order to calculate corresponding polymeric product properties. The raw materials may also be chosen based on commercial or logistical considerations.

In principle, any raw material used for polymeric production may be specified by the formulation portions, even if it is not present in the finished polymeric product. According to a further preferred embodiment of the method, the user-selected raw materials comprise an isocyanate and a polyol. The user-selected raw materials may also comprise a plurality of isocyanates and/or a plurality of polyols. The user-selected raw materials may also comprise a blowing agent. Preferably, the user-selected raw materials further comprise a chain extender, a cross linker, a catalyst for accelerating the formation of foam, a flame retardant, a pigment and/or a surfactant.

The production parameters can be provided not only by having one particular set value for each parameter, but also providing a plurality of set values or a value range for each parameter. In this context, a preferred embodiment of the method is characterized in that the set of production parameters comprises at least one portion bracket for a respective raw material of the user-selected raw materials, which portion bracket defines a subrange within a maximum portion range predefined in the computer system for that raw material, and that the computer system applies the user production parameters to the prediction model such that for a plurality of portion values within each portion bracket resultant product properties are calculated. Thus, when such a portion bracket is provided, also a plurality of resultant product properties corresponding to a plurality of portion values in the portion bracket is calculated. Preferably, the set of production parameters comprise a plurality of portion brackets for respective raw materials of the user-selected raw materials. When such a respective portion bracket is provided for a plurality of raw materials, then accordingly the plurality of resultant product properties may correspond to a set of combinations of the portion values from the plurality of portion brackets. There may also be several portion brackets for one and the same raw material. Accordingly, it is preferred that the set of production parameters comprises at least for one raw material of the user-selected raw materials a plurality of non-overlapping portion brackets.

In principle, the plurality of portion values within the portion bracket may be determined in an arbitrary manner. One possibility is to sweep the portion bracket with a given resolution or granularity. Thus, according to a preferred embodiment of the method, the set of production parameters comprises a portion resolution for each portion bracket, which portion resolution defines a step value for varying a portion value within the respective portion bracket and the computer system applies the user production parameter to the prediction model such that the plurality of portion values within each portion bracket is determined by varying the portion values according to the step value. Such a parameter resolution may also differ from portion bracket to portion bracket. Preferably, the respective parameter resolution of two portion brackets for the same raw material is different.

The above machine process properties may in principle relate to any setting applied to an arrangement, machine or plant involved in the production of polymeric product or any constant characteristic describing such an arrangement, machine or plant. In particular, the machine process properties may comprise machine process settings for variably adjusting the operation of a machine in the production of a polymeric product. According to a further preferred embodiment of the method, the machine process properties comprise a component temperature, a mixing time, a mixing proportion, a tool temperature, a discharge capacity and/or a line speed. All the described machine process properties are in particular for the polymeric production.

A plurality of set values or a value range may also be provided for the process properties. A preferred embodiment of the method is characterized in that the set of production parameters comprises at least one property bracket for a respective process property, which settings bracket defines a subrange within a maximum properties range predefined in the computer system for that process property, and that the computer system applies the user production parameters to the prediction model such that for a plurality of property values within each property bracket resultant product properties are calculated. Preferably, the set of production parameters comprise a plurality of properties brackets for respective process properties. Also for the process properties, when such a properties bracket is provided for a plurality of process properties, then accordingly the plurality of polymeric product properties may correspond to a combination of the property values from the plurality of properties brackets. Preferably, the set of production parameters comprises at least for one process property a plurality of non-overlapping properties brackets.

According to a preferred embodiment of the method, the set of production parameters comprises a properties resolution for each properties bracket, which properties resolution defines a step value for varying a properties value within the respective properties bracket and the computer system applies the user production parameter to the prediction model such that the plurality of properties values within each properties bracket is determined by varying the properties values according to the step value. This permits performing a sweep through the properties bracket in the same way as described above for the portion bracket.

Preferably, the respective properties resolution of two properties brackets for the same process property is different.

According to a further preferred embodiment of the method, the computer system identifies the production parameters from the specified set of production parameters associated with the proximity value corresponding to the highest conformity with the user product parameters. In this way, a computerized evaluation, which may be based on an in principle arbitrarily complex metric, is performed on the specified set of production parameters. It is further preferred that the computer system outputs the resultant product properties and the determined at least one proximity value.

In principle, the prediction model can be arrived at in any manner and generated based on any considerations. However, it is particularly helpful when the prediction model can be based on a preferably large amount of historic formulation data. Thus, a preferred embodiment of the method is characterized in that on the computer system a formulation database is provided comprising test entries for a respective polymeric formulation, wherein each test entry comprises polymeric product properties data associated with that polymeric formulation and comprises formulation portions data specifying raw material portions used for the production of that polymeric formulation and comprises processing parameters data specifying process properties during the production of that polymeric formulation.

The formulation database may either be a single database or may be a system of several databases, with different kinds of information stored in each of the several databases.

The solidified plastic foam product properties data may comprise measurement data measured from the polymeric formulation or products from it. In other words the measurement data may have been obtained by a test of the polymeric formulation. A database of historic lab and large-scale production runs of polymeric formulations may provide such data.

Further, the polymeric product properties data may comprise measurement circumstance data describing the measurement process applied for obtaining the measurement data. This measurement circumstance data may describe measurement apparatus properties, in particular measurement apparatus settings, applied when obtaining the measurement data. The measurement circumstance data may also comprise ambient properties, which may include temperature and pressure, when obtaining the measurement data. Further, the measurement data may also comprise usage properties of the polymeric product from which the measurement data was obtained, which usage properties describe the usage of that polymeric product prior to obtaining of the measurement data. For example, these usage properties may comprise a storage duration of the polymeric product from which the measurement data was obtained and ambient properties during storage of the polymeric product from which the measurement data was obtained.

However, missing values in the polymeric product properties data may occur. Preferably, the polymeric product properties data comprises reconstructed data. The reconstructed data therefore serves to fill such missing values. Such reconstructed data may be data calculated by applying analytical formulas. Such reconstructed data may also be determined based on interpolation or extrapolation, on statistical analysis and/or on expert knowledge. Ways to fill missing values could be using statistical analyses and/or expert knowledge. Statistical analyses may provide median, average value, expectation values, minimum or maximum values based on the given values for each parameter. PUR expert knowledge comprises knowledge of similar formulations with corresponding production parameters and of chemical properties.

The advantage of using historical and measured data is that a prediction model based on them does not need to rely on theoretical assumptions which may turn out to be inaccurate. Preferably, the prediction model is generated by executing a numerical analysis program on the formulation database. In principle, any kind of numerical analysis may be used to generate the prediction model. Advantageously, the numerical analysis program preferably comprises a multivariate analysis, machine learning, deep learning and/or artificial intelligence.

The manner in which the prediction model calculates the polymeric product properties based on the foam production parameters may generally be of any kind. According to a preferred embodiment of the invention, the prediction model defines a multi-variable functional relationship with the production parameters as input parameters and the polymeric product properties as output parameters. Here it is further preferred that when the computer system generates the prediction model, the dependency between the input parameters and the output parameters is based on a fitting algorithm to match the prediction model to the test entries of the formulation database. For this fitting, any kind of fitting algorithm may be used. It is to be noted that the prediction model need not in fact be optimal in any sense with respect to the test entries of the formulation database.

In a further preferred embodiment, the prediction model is, in particular automatically, regenerated when a change in the formulation database occurs, in particular when a new test entry is added to the formulation database and/or when new data is added to an existing test entry of the formulation database. Therefore, any ongoing new measurement continually adds to the quality of the prediction model.

According to a preferred embodiment of the invention, the prediction model is configured for calculating polymeric product properties also based on product history data, which product history data describes a history of a polymeric product produced according to the production parameters. The additional consideration of such a product history is based on the realization that the polymeric product properties of a polymeric product may change in time from their initial values and in particular may change depending on ambient variables or usage during the time since production. For example, prolonged storage of the polymeric product in high temperatures may result in the degradation of certain polymeric product properties. The same may occur if and when the polymeric product undergoes mechanical or chemical stresses for any periods of time. Accordingly, the product history data preferably comprises ambient variables around the polymeric product or mechanical and/or chemical effects applied to the polymeric product. In particular, the ambient variables and/or the mechanical and/or chemical effects form a respective distribution which variable during a given time span. In this way, the polymeric product properties may not only be predicted for the situation right out of production, but also for some time after production and during which time the polymeric product may have changed due to external influences.

One advantage of analyzing both the formulation portions and the processing parameters of the formulation database in a combined and therefore unified way is that specific relationships between one or more parameters among the formulation portions on the one hand and the processing parameters on the other hand may be determined. Such relationships may remain undiscovered if these are analyzed only separately. Consequently, according to a further preferred embodiment of the invention, when the computer system generates the prediction model, the computer system executes a dimension reduction which involves both a formulation portion dimension and processing parameter dimension. Preferably, the execution of the dimension reduction comprises a principal component analysis in order to determine a set of principal components with fewer principal components than the foam production parameters and that at least one determined principal component comprises both a formulation portion dimension and a processing parameter dimension.

In general, when generating the prediction model based on numerical analysis of the data from the formulation database, the prediction model usually becomes more accurate the more data is used for the prediction model. However, it may be that only a certain parameter region is of relevance for the specified user product parameters. In such situations, the prediction model for that parameter region may be more accurate when the data basis for the prediction model is restricted to within a proximity bracket for the relevant parameter. In this way, outliers outside the proximity bracket are prevented from influencing the prediction model in the relevant range. Therefore, a preferred embodiment of the method is characterized in that the user input comprises at least one properties proximity bracket for a respective process property, which properties proximity bracket defines a subrange within a maximum properties range predefined in the computer system for that process property and that, when the computer system generates the prediction model, for determining a functional relationship with that process property as input parameter, only test entries with that process property within the proximity bracket are considered, It is further preferred that the properties proximity bracket extends beyond a properties bracket for the same process property.

For different reasons it may be advantageous to identify from the formulation database that formulation which most closely exhibits the properties specified by the user product parameters. The identification of such a formulation may enable the user to formulate the user production parameters such that matching resultant product properties are more easily found. According to a preferred embodiment of the method, the computer system determines at least one formulation candidate based on a comparison of the user product parameters with the polymeric product properties data of the test entries of the formulation database. Preferably, the computer system outputs the at least one formulation candidate.

The computer system according to the invention is for determining polymeric product properties. The computer system according to the invention comprises a computer arrangement and a prediction model for calculating polymeric product properties based on production parameters stored on the computer arrangement, which production parameters comprise formulation portions specifying raw material portions for polymeric production and comprise processing parameters specifying process properties during polymeric production. In the computer system according to the invention, the computer arrangement is configured to receive user input comprising user production parameters specifying a set of production parameters, wherein the user input comprises user product parameters specifying polymeric product properties and comprises a proximity metric for quantifying conformity with the user product parameters. In the computer system according to the invention, the computer arrangement is further configured to apply the user production parameters to the prediction model to calculate resultant product properties and the computer arrangement is configured to apply the proximity metric to the resultant product properties with respect to the user product parameters so as to determine at least one proximity value indicating a match between the user product parameters and the resultant product properties.

The computer arrangement may comprise one or more physical computer devices. In particular, the computer arrangement may comprise an arrangement for providing cloud computing services.

Preferred embodiments, features and advantages of the computer system according to the invention correspond to those of the method according to the invention and vice versa.

Further advantageous and preferred features are discussed in the following description with respect to the Figures. In the following it is shown in FIG. 1 an illustration of the functioning principle of an embodiment of the method according to the invention and in FIG. 2 a computer system according to an embodiment of the invention.

The method according to the invention is used to determine polymeric product properties 1, which in the present example are polyurethane product properties. These polymeric product properties 1 comprise here a wide range of physical or chemical properties of a polyurethane product, such as density, compressive strength, dimensional stability, thermal resistance, fire performance and emissions. In FIG. 1, the totality of these polymeric product properties 1 is illustrated in a simplified way along one axis—the z-axis—only for the sake of clarity. In reality, the polymeric product properties 1 correspond to an array of values and are therefore multi-dimensional.

More generally, a user of the method according to the invention is seeking to identify a recipe for producing a polymeric product, described here in terms firstly of formulation portions 2, which describe the respective proportion of raw material used in the production of the polyurethane product. In analogy to the polymeric product properties 1, also the formulation portions 2 are illustrated in a simplified way along one axis only, which is here the x-axis, even though the formulation portions 2 are multidimensional.

This recipe is described secondly in terms of processing parameters 3, which determine the settings, i.e. variable properties, as well as the predefined and therefore constant properties, such as physical dimensions, of a machine, either of a smaller scale in a lab or of a larger scale in a factory, used to produce a polyurethane product from the ingredients according to the formulation portions 2. Like the polymeric product properties 1 and the formulation portions 2, also the processing parameters 3 are illustrated in a simplified way along one axis only, which is here the y-axis, even though also the processing parameters 3 are multi-dimensional.

The formulation portions 2 and the processing parameters 3 together form the production parameters defining such a recipe, though it is possible that the production parameters comprise additional information. The user strives to identify particular production parameters such that the resultant polyurethane product exhibits physical characteristics in accordance with user product parameters 5. The user product parameters 5 specify target product properties that are here pre-defined. Such user product parameters 5 may arise from a specific customer request or may be determined such that the polyurethane product can be used in a specific component or in some specific way for a larger arrangement.

Like the polymeric product properties 1, the user product parameters 5 are here illustrated as a single value along the one-dimensional axis corresponding to the polymeric product properties 1, even though in practice they extend in several directions. Moreover, and also in deviation from the illustration of FIG. 1 the user product parameters 5 do not specify just a single desired value of polymeric product properties 1, but rather a value bracket. In other words, any value within that value bracket is deemed within the specification according to the user product parameters 5. Associated with the user product parameters 5 is a proximity metric which defines a degree of compliance with the user product parameters 5. Such a degree of compliance may be quantified potentially even if the polymeric product properties 1 do not exactly match the user product parameters 5. In that case, the degree of compliance may be expressed by a number. In the present example, the proximity metric is a simple function which is true when the polymeric product properties 1 are within the value bracket defined by the user product parameters 5 and false when they are outside.

Figure 2:
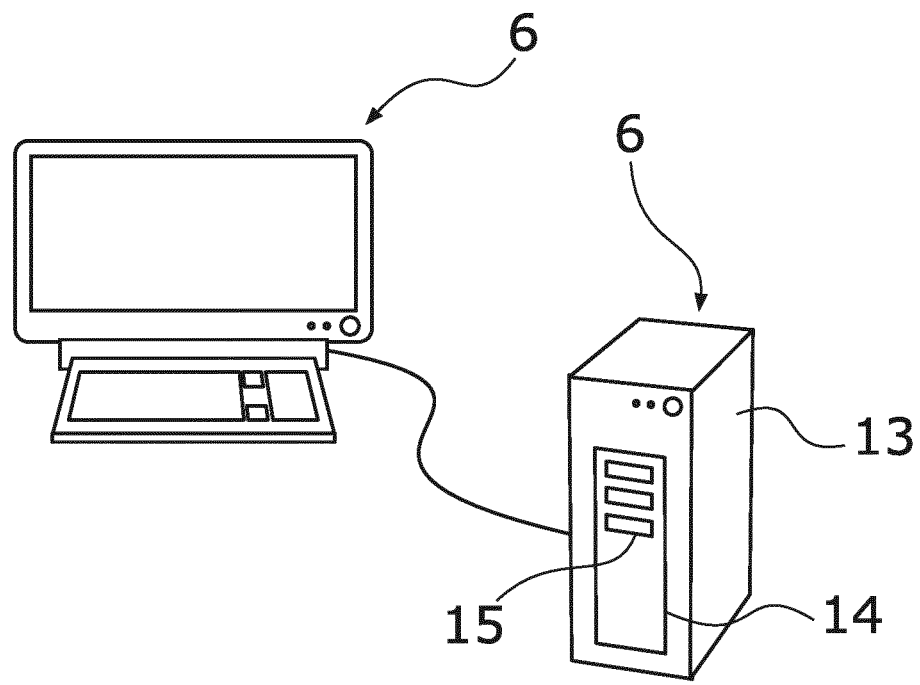

The user now provides user input to the computer arrangement 6, shown in FIG. 2, of a computer system. In present example, the computer arrangement 6 is a single computer device. That user input comprises the above user product parameters 5, the above proximity metric and in addition user production parameters 4. These user production parameters 4 comprises a set of production parameters, which are here polyurethane production parameters, which set may be understood to present candidate production parameters from which the specific polyurethane production parameters are to be identified which come closest to the user product parameters 5 as quantified by the proximity metric.

The computer arrangement 6 of the computer system utilizes a prediction model 7 stored on the computer arrangement 6 in order to calculate polymeric product properties 1 based on the polyurethane production parameters of the user production parameters 4. This prediction model 7 is shown in FIG. 1 in a simplified manner as a function with a one-dimensional output, corresponding to the product properties 1, and a two-dimensional input consisting of the formulation portions 2 and the processing parameters 3. In reality, both the input and the output of the prediction model 7 can be multidimensional.

For the user production parameters 4, the computer arrangement 6 of the computer system now calculates the resultant product properties 8 based on the prediction model 7 and in particular by applying the set of polyurethane production parameters of the user production parameters 4 to the prediction model 7. In other words, each member within the set of polyurethane production parameters forms the input for the function defined by the prediction model 7 and the resultant product properties 8 form the corresponding output. Thus, for each polyurethane production parameters from the set, corresponding resultant product properties 8 are calculated. For each such corresponding resultant product properties 8 the proximity metric is applied to determine a corresponding proximity value, which in the present embodiment amounts to a determination whether or not the resultant product properties 8 are within the user product parameters 5 or not.

In this way, the user can check whether and which one of the polyurethane production parameters from the user production parameters 4 matches the desired user product parameters 5. When a proximity metric is used which more accurately quantifies a distance to the user product parameters 5, even if none of the resultant product properties 8 matches the user product parameters 5, at least the polyurethane production parameters which come closest to the user product parameters 5 can be identified, which in turn can then be a starting point for further improvement.

As can be seen in FIG. 1, the user production parameters 4 comprise a portion bracket 9 in which portion values of formulation portions 2 are defined. Again, what in reality corresponds to different portion brackets for different raw material portions is shown in a simplified manner for one dimension. These portion values may either be set by explicit choice or by defining a portion resolution which divides the portion bracket 9 equally according to the portion resolution. Thus, the portion bracket 9 may be swept according to the resolution. Several portion brackets 9 with respective different portion resolution may also be defined. In the present case, individual portion values are not illustrated in FIG. 1 but instead it is assumed that a resolution to finely sweep the portion bracket 9 is defined.

Equally, the user production parameters 4 comprise a properties bracket 10 in which property values of processing parameters 3 are defined. Also these property values may be set by explicit choice or by the definition of a properties resolution analogous to the portion resolution, with the illustration in FIG. 1 being a one-dimensional simplification as described above for the portions bracket 9. Again, individual setting values are not illustrated but instead a sweep with an appropriately fine resolution is assumed. The two-dimensional area 11 corresponding to the combined sweep of the portion bracket 9 and the properties bracket 10 is shown in FIG. 1. This area 11 corresponds to the input values for the resultant product properties 8.

The computer arrangement 6 of the computer system may then calculate the resultant product properties 8 for all combination of portion values and property values in the portion bracket 9 and the properties bracket 10, respectively. In the present case and as shown in FIG. 1, there is a region 12 of combinations of portion values and property values resulting in the calculation of resultant product properties 8 which match the user product parameters 5. The combinations of these region 12 as well as the resultant product properties 8 are identified by the computer arrangement 6 and output to the user.

The computer arrangement 6 comprises a memory unit 13 in which a formulation database 14 is stored with a plurality of test entries 15 for polyurethane formulations, which has been compiled from historic data concerning the production and testing of polyurethane products. The prediction model 7 has been generated by the computer arrangement 6 performing a multivariate analysis, including a dimension reduction method, e.g. principal component analysis, and a fitting step, on the data of the formulation database 14. In FIG. 1, test polyurethane product properties data 16 for some exemplary test entries 15 of the formulation database 14 are shown. As can be seen, the prediction model 7 substantially corresponds to a best fit approximation for the test polyurethane product properties data 16 of the exemplary test entries 15.

The invention claimed is:

1. A method for the production of a polymeric product having determined polymeric product properties, comprising:

providing a prediction model for calculating polymeric product properties based on production parameters on a computer system, the production parameters comprising formulation portions specifying raw material portions for polymeric production and comprising processing parameters specifying process properties during polymeric production, providing user input to the computer system, which user input comprises user production parameters specifying a set of production parameters, user product parameters specifying polymeric product properties and a proximity metric for quantifying conformity with the user product parameters, applying, by the computer system, the user production parameters to the prediction model to calculate resultant product properties, applying, by the computer system, the proximity metric to the resultant product properties with respect to the user product parameters to determine at least one proximity value indicating a match between the user product parameters and the resultant product properties, providing, on the computer system, a formulation database comprising test entries for a respective polymeric formulation, wherein each test entry comprises polymeric product properties data associated with that polymeric formulation and comprises formulation portions data specifying raw material portions used for the production of that polymeric formulation and comprises processing parameters data specifying process properties during the production of that polymeric formulation, generating the prediction model by executing a numerical analysis program, wherein the set of production parameters comprises at least one properties bracket for a respective process property, which properties bracket defines a subrange within a maximum properties range predefined in the computer system for that process property, applying, by the computer system, the user production parameters to the prediction model such that for a plurality of property values within each property bracket resultant product properties are calculated, identifying, by the computer system, a recipe for preparing a polymeric product having the calculated resultant product properties, and operating a machine in the production of the polymeric product having the calculated resultant product properties according to the recipe.

2. The method according to claim 1, wherein the formulation portions concern a plurality of user-selected raw materials from a list of raw materials predefined in the computer system, thereby defining combinations of the user-selected raw materials for a polymeric formulation, and that the computer system applies the user production parameters to the prediction model such that for the defined combinations of the user-selected raw materials resultant product properties are calculated.

3. The method according to claim 2, wherein the user-selected raw materials comprise an isocyanate and a polyol, in particular also a blowing agent, preferably, further comprise a chain extender, a cross linker, a catalyst for accelerating the formation of foam product, a flame retardant, a pigment and/or a surfactant.

4. The method according to claim 2, wherein the set of production parameters comprise at least one portion bracket for a respective raw material of the user-selected raw materials, which portion bracket defines a subrange within a maximum portion range predefined in the computer system for that raw material, and that the computer system applies the user production parameters to the prediction model such that for a plurality of portion values within each portion bracket resultant product properties are calculated, preferably, that the set of production parameters comprises at least for one raw material of the user-selected raw materials a plurality of non-overlapping portion brackets.

5. The method according to claim 4, wherein the set of production parameters comprise a portion resolution for each portion bracket, which portion resolution defines a step value for varying a portion value within the respective portion bracket and that the computer system applies the user production parameters to the prediction model such that the plurality of portion values within each portion bracket is determined by varying the portion values according to the step value, preferably, that the respective parameter resolution of two portion brackets for the same raw material is different.

6. The method according to claim 1, wherein the processing parameters comprise machine processing parameters specifying machine process properties during polymeric production, preferably, the machine process properties comprise a component temperature, a mixing time, a mixing proportion, a tool temperature, a discharge capacity and/or a line speed.

7. The method according to claim 1, wherein the set of foam production parameters comprises at least for one process property a plurality of nonoverlapping properties brackets.

8. The method according to claim 7, wherein the set of production parameters comprise a properties resolution for each properties bracket, which properties resolution defines a step value for varying a properties value within the respective properties bracket and that the computer system applies the user production parameters to the prediction model such that the plurality of properties values within each properties bracket is determined by varying the properties values according to the step value, preferably, that the respective properties resolution of two properties brackets for the same process properties is different.

9. The method according to claim 1, wherein the computer system identifies the production parameters from the specified set of production parameters associated with the proximity value corresponding to the highest conformity with the user product parameters, preferably, that the computer system outputs the resultant product properties and the determined at least one proximity value.

10. The method according to claim 1, wherein, the numerical analysis program further comprises multivariate analysis and/or machine learning.

11. The method according to claim 10, wherein the prediction model defines a multi-variable functional relationship with the production parameters as input parameters and the polymeric product properties as output parameters, preferably, that when the computer system generates the prediction model, the dependency between the input parameters and the output parameters is based on a fitting algorithm to match the prediction model to the test entries of the formulation database.

12. The method according to claim 11, wherein when the computer system generates the prediction model, the computer system executes a dimension reduction which involves both a formulation portion dimension and processing parameter dimension, preferably, that the dimension reduction comprises a principal component analysis in order to determine a set of principal components with fewer principal components than the foam production parameters and that at least one determined principal component comprises both a formulation portion dimension and a processing parameter dimension.

13. The method according to claim 11, wherein the user input comprises at least one properties proximity bracket for a respective process property, which properties proximity bracket defines a subrange within a maximum properties range predefined in the computer system for that process property and that, when the computer system generates the prediction model, for determining a functional relationship with that process property as input parameter, only test entries with that process property within the proximity bracket are considered, preferably, that the properties proximity bracket extends beyond a properties bracket for the same process property.

14. The method according to claim 10, wherein the computer system determines at least one formulation candidate based on a comparison of the user product parameters with the polymeric product properties data of the test entries of the formulation database, preferably, that the computer system outputs the at least one formulation candidate.

15. A system for determining polymeric product properties of a polymeric product, the system comprising a computer arrangement and a prediction model for calculating polymeric product properties based on production parameters stored on the computer arrangement, the production parameters comprising formulation portions specifying raw material portions for polymeric production and comprising processing parameters specifying process properties during polymeric production, wherein the computer arrangement is configured to receive user input comprising user production parameters specifying a set of production parameters, the user input comprising user product parameters specifying polymeric product properties and comprising a proximity metric for quantifying conformity with the user product parameters, and further configured to apply the user production parameters to the prediction model to calculate resultant product properties and the computer arrangement configured to apply the proximity metric to the resultant product properties with respect to the specified user product parameters so as to determine at least one proximity value indicating a match between the user product parameters and the resultant product properties, wherein the set of production parameters comprises at least one properties bracket for a respective process property, which properties bracket defines a subrange within a maximum properties range predefined for that process property, that the user production parameters are applied to the prediction model such that for a plurality of property values within each property bracket resultant product properties are calculated, the computer arrangement configured to identify a recipe for preparing a polymeric product having the calculated resultant product properties, wherein the system further comprises a machine configured to be operated to produce the polymeric product having the calculated resultant product properties according to the recipe.

* * * * *